United States Patent
Yamada et al.

[11] Patent Number: 5,800,545
[45] Date of Patent: Sep. 1, 1998

[54] ARTIFICIAL HAIR FOR IMPLANTATION AND PROCESS FOR PRODUCING THE SAME

[76] Inventors: Shiro Yamada, 7-1-606, Mita 2-chome, Minato-ku, Tokyo 108; Yoshito Ikada, 182, Gokasyo-hirookadani 2-chome, Uji-shi, Kyoto 611, both of Japan

[21] Appl. No.: 776,643
[22] PCT Filed: Jun. 4, 1996
[86] PCT No.: PCT/JP96/01501
  § 371 Date: Feb. 5, 1997
  § 102(e) Date: Feb. 5, 1997
[87] PCT Pub. No.: WO96/40301
  PCT Pub. Date: Dec. 19, 1996

[30] Foreign Application Priority Data

Jun. 7, 1995 [JP] Japan ........................ 7-163089
Mar. 19, 1996 [JP] Japan ........................ 8-089018

[51] Int. Cl.⁶ .................................................. A61F 2/10
[52] U.S. Cl. .......................... 623/15; 623/11; 427/2.1; 427/2.24
[58] Field of Search ............... 623/11, 15; 604/266; 427/201, 2.24

[56] References Cited

U.S. PATENT DOCUMENTS

| | | | |
|---|---|---|---|
| 4,828,561 | 5/1989 | Woodroof | 623/15 |
| 5,005,518 | 4/1991 | Yamada . | |
| 5,010,009 | 4/1991 | Steele et al. | 623/15 |
| 5,028,597 | 7/1991 | Kodama et al. | 623/11 |
| 5,263,992 | 11/1993 | Guire | 604/266 |
| 5,376,400 | 12/1994 | Goldberg et al. | 427/2.24 |

FOREIGN PATENT DOCUMENTS

2-251604 10/1990 Japan .
4-041180 7/1992 Japan .

*Primary Examiner*—Paul B. Prebilic
*Attorney, Agent, or Firm*—Browdy and Neimark

[57] ABSTRACT

An artificial hair having a physiologically active surface which is formed by a such manner that protein (collagen) molecules are bonded chemically to the graft-polymerized chains introduced onto the surface of the artificial hair. When the artificial hair is implanted into a human body skin, the collagen layer 11 fixed to the surface of the artificial hair having a root part 12 is integrally assimilated and bonded to collagens in the epidermis 4, the corium layer 5, the subcutaneous tissue 6 and the galea 7, whereby the artificial hair can be firmly fixed. Thus, this artificial hair exhibits a low infection rate, a high success rate and cannot be accompanied by down-growth phenomenon.

11 Claims, 2 Drawing Sheets

ARTIFICIAL HAIR FOR IMPLANTATION AND PROCESS FOR PRODUCING THE SAME

This application is a national stage 35 USC 371 application of PCT/JP96/01501 filed Jun. 4, 1996.

TECHNICAL FIELD

The present invention relates to an artificial hair which is suitable for direct implantation into the human skin, and to a process for producing the same.

BACKGROUND ART

There are many conventionally proposed artificial hairs adapted for direct implantation into human skin. Some of these artificial hairs put into practical use include those having a loop-shaped hair root part developed by one of the present inventors (see Japanese Patent Publication No. 8770/91 and U.S. Pat. No. 4,793,368).

FIG. 2 shows a skin section immediately after implantation of the artificial hair developed by the present inventors. The artificial hair is formed of a monofilament 1 of a polyester fiber and has a loop-shaped hair root part formed at its base. If an implanting needle is brought into engagement with the loop-shaped root part 2 to hold the artificial hair, and stuck into the skin, the loop of the root part 2 is deeply implanted so as to come into contact with the deepest portion of a subcutaneous tissue 6, i.e., the galea 7. A hook 13 prevents the implanted artificial hair from falling out. In FIG. 2, reference character 3 designates the horny layer of the skin; reference character 4 designates the skin epidermis; and reference character 5 designates the corium layer.

The human skin tissue has the ability, if the foreign matter is inserted into the human skin tissue to form a fibrous connective tissue, to isolate such foreign matter from the subcutaneous tissue 6. As for the implantation of artificial hair, after a given period of time has elapsed after such implantation, fibrous connective tissue 8 is produced within and outside the root part 2, as shown in FIG. 3. The fibrous connective tissue 8 would soon become fused to the galea 7, which is firm connective tissue located at the deepest portion of the head skin, to rigidly fix the loop-shaped root part 2 to the galea 7 by such fibrous connective tissue 8, whereby the artificial hair becomes firmly fixed to the head skin.

However, the epidermis 4, which is flat immediately after implantation as shown in FIG. 2, often then begins to grow downwardly to the middle of the corium layer 5 along the length of the artificial hair in an area where the artificial hair passes through the epidermis 4, and ultimately in some cases, a large hair infundibulum 9 may be formed, as shown in FIG. 3. This phenomenon is called down-growth, and causes a problem that the skin around the implanted artificial hair appears to be depressed, whereby secreted sebum collects in the hair infundibulum 9 and becomes oxidized into a black color, resulting in an unattractive appearance.

On the other hand, there is an artificial hair conventionally proposed and known for a long time, wherein a material assimilatable to the human skin tissue is deposited around the artificial hair to be implanted, thereby enhancing the success rate of the hair implantation (see U.S. Pat. No. 3,596,292). This prior art describes the use of a synthetic human body alternative substance, which may be a reticulated urethane foam synthetic material deposited on a surface of a root part of the artificial hair, or hydrogel of polyacrylic acid or polyvinyl alcohol applied to the surface of the root part. The thin layer or film of synthetic human body alternative substance is assimilated into the subcutaneous tissue to fix the artificial hair.

In the artificial hair described in U.S. Pat. No. 3,596,292, the assimilation of the artificial hair to the subcutaneous tissue is achieved by the thin layer or film of the synthetic human body alternative substance. However, the artificial hair and the thin layer or film of the human body alternative substance are merely physically bonded each other and, hence, the human body tissue still discerns the artificial hair as a foreign matter. Thus, the artificial hair often becomes discharged by a foreign matter reaction and easily falls out, and a down-growth similar to that described above in connection with the Japanese Patent Publication No. 8770/91 occurs; and, as a result, microorganisms may intrude into the body skin through a produced gap, so that infection is liable to occur.

Another problem is that the bonding force is reduced due to a change, with the passage of time, of an adhesive used for bonding the artificial hair to the layer of the synthetic human body alternative substance or due to some other cause, and as a result the artificial hair is liable to fall out. Particularly, since the hydrogel is merely applied to the artificial hair surface, the hydrogel, when the artificial hair has been stuck into the human body, becomes swelled, resulting in a reduced bonding force, causing the artificial hair to easily fall out.

There is a method proposed by one of the present inventors, in which the surface of a polymer material is activated by an electrical discharge treatment to fix a protein in order to modify the surface of the polymer material to enhance biological compatibility (see Japanese Patent Publication No. 41180/92).

The method described in Japanese Patent Publication No. 41180/92 activates the surface of the polymer material by the electrical discharge treatment, and graft-polymerizes a radical polymerizable monomer to activate the surface of the polymer material so as to fix a protein to the surface of the graft-polymerized polymer material. In the description of the embodiment, a sheet-like polymer material is used, but a fine monofilament like an artificial hair is not discussed.

It is also known, and backs up the foregoing, that an electrical discharge such as plasma discharge, corona discharge, glow discharge, application of ionizing radiations and the like, is used to activate the surface of the polymer material.

However, if the surface of the artificial hair for implantation is treated by electrical discharge such as plasma discharge, corona discharge, glow discharge and the like, there is a possibility that such treatment may cause deterioration of the surface of the artificial hair. When ionizing radiation is applied, there is a problem that the absolute amount of radicals produced is too small. When any of these electrical discharge treatments is used, it is extremely difficult to modify the entire peripheral surface of the monofilament all over due to the inherent limitations of the apparatus, such as the use of a vacuum apparatus to accomplish this treatment.

It is a first object of the present invention to provide an artificial hair for implantation, in which defects of the prior art artificial hair are overcome, which exhibits a high success rate and which is accompanied by no down-growth phenomenon.

It is a second object of the present invention to provide a process for producing an artificial hair for implantation in an inexpensive manner and by a simple operation, which hair exhibits a low infection rate and a high success rate and which is accompanied by no down-growth phenomenon.

DISCLOSURE OF INVENTION

To achieve the above objects, according to the present invention, there is provided an artificial hair for implantation, which is formed from a monofilament of a synthetic fiber such as polyethylene, polypropylene, polyester, polyamide, acrylic and fluorine-based fibers, wherein the artificial hair includes a biologically compatible layer which is formed by fixing protein to a surface of the artificial hair by a chemical bonding.

Above mentioned biologically compatible layer is formed by the chemical bonding the protein molecules to the surface of the artificial hair through the graft-polymerized chains introduced into the surface of the artificial hair by a graft polymerization of a radical-polymerizable monomer such as a carboxyl group-containing monomer or a sulfonic group-containing monomer.

In addition, according to the present invention, there is provided a process for producing an artificial hair for implantation, formed from a monofilament of a synthetic fiber such as polyethylene, polypropylene, polyester, polyamide, acrylic and fluorine-based fibers, the process comprises the steps. of introducing graft-polymerized chains onto the artificial hair surface, chemically bonding protein molecules to the graft-polymerized chains, and cross-linking the protein molecules chemically bonded to the graft-polymerized chains to one another or to an additionally added protein to form a biologically compatible layer on the surface of the artificial hair.

In a still further aspect of the present invention, there is provided a process for producing the artificial hair for implantation which is formed from the monofilament of the synthetic fiber such as polyethylene, polypropylene, polyester, polyamide, acrylic and fluorine-based fibers, the process comprises the steps of introducing the graft-polymerized chains onto the surface of the artificial hair by means of irradiation of an electromagnetic wave which produces free radicals, such as ionizing radiation or ultraviolet rays in a condition in which the artificial hair has been immersed into a solution containing the radical polymerizable monomer; chemical bonding the protein molecules to the graft-polymerized chains introduced on the surface of the artificial hair by utilizing a covalent bonding reaction or an ionic bonding reaction; and cross-linking the protein molecules chemically bonded to the graft-polymerized chains to one another, or to additionally added protein molecules to form the biologically compatible layer on the surface of the artificial hair.

BRIEF DESCRIPTION OF DRAWINGS

To explain this invention in further detail, some examples are disclosed.

Figure 1:
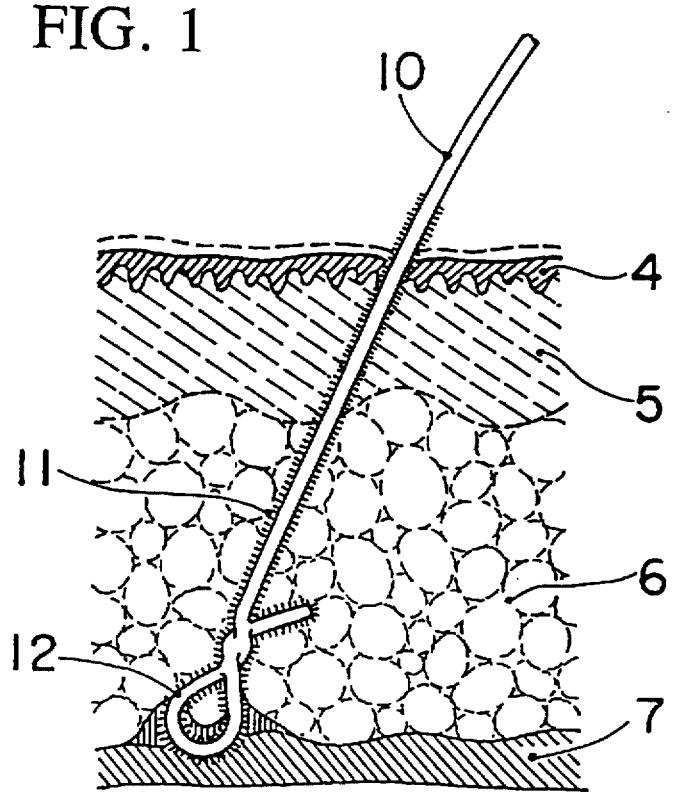
FIG. 1 is a sectional view of an artificial hair in a state after lapse of a given period of time from the implantation thereof.
Figure 2:
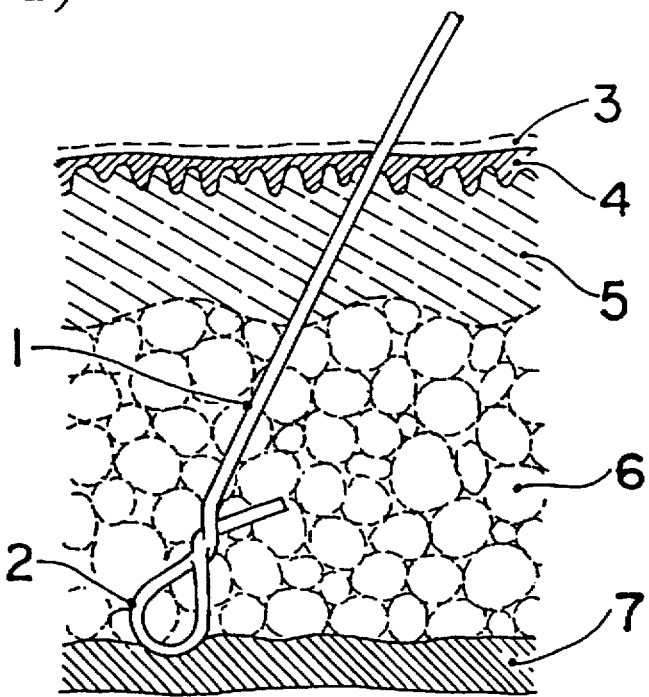
FIG. 2 is a sectional view of the prior art artificial hair in a state immediately after the implantation thereof.
Figure 3:
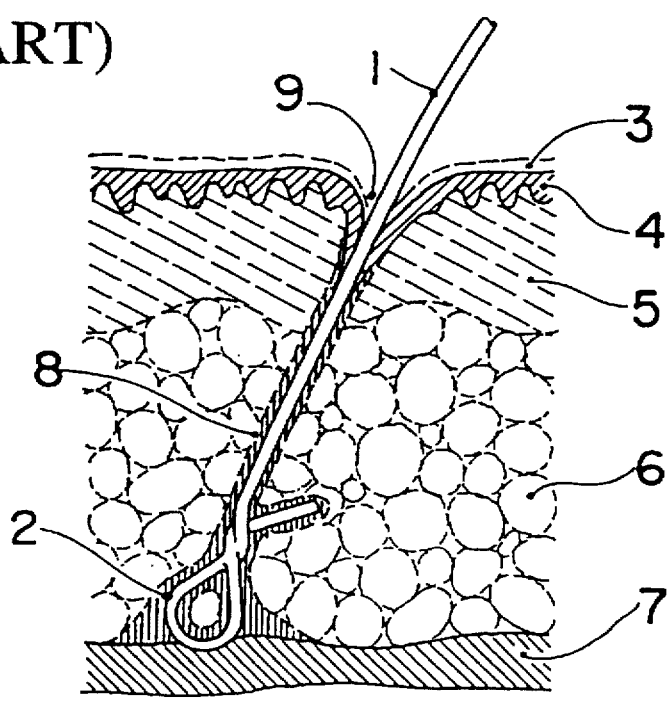
FIG. 3 is a sectional view of the prior art artificial hair in a state after lapse of a given period of time from the implantation thereof.

Typical of the polyester fiber is a polyethyleneterephthalate fiber (PET) produced by melt-spinning of polyethyleneterephthalate.

Typical of the polyamide fiber are those produced by spinning of linear aliphatic polyamides, and a monofilament of nylon 6 is particulary preferred.

Preferred acrylic fibers are fibers produced by spinning of polyacrylonitrile, particularly, a copolymer of 50% or more of acrylonitrile with acrylic ester, vinyl acetate, acrylamide or methacrylic ester.

Examples of the fluorine-based fibers are those produced by spinning of polytetrafluoroethylene, polychloro-trifluoroethylene, tetrafluoroetylene-hexafluoropropylene copolymer, polyvinylidene fluoride and the like; particularly, a monofilament formed of polytetrafluoroethylene as a main constituent is preferred.

To fix the protein to the surface of the artificial hair for implantation formed from the monofilament of the synthetic fiber such as polyethylene, polypropylene, polyester, polyamide, acrylic and fluorine-based fibers, the surface of the artificial hair may be subjected to a graft-modifying process, whereby the graft-polymerized chains can be introduced into the surface, and the protein can be chemically bonded to the graft-polymerized chains. Thus, the protein is bonded firmly and retained in the artificial hair surface over a long period.

To subject the surface of the artificial hair to the graft-modifying treatment to introduce the graft-polymerized chains onto the surface, an active species to effect or facilitate radical-graft-polymerization may be introduced onto the artificial hair surface, so that a radical-polymerizable monomer such as a carboxyl group-containing monomer or a sulfonic group-containing monomer may be bonded by a graft polymerization occurring under the action of the active species.

To produce the active species acting as a polymerization initiator for the graft polymerization, it is necessary to activate carbon atoms in the carbon chains of the high-molecular-weight compound forming the artificial hair, thereby producing free radicals. To produce such free radicals, the artificial hair surface may be activated by an electrical discharge such as plasma discharge, corona discharge, glow discharge, ion discharge and the like. However, as these electrical discharge treatments are carried out in vacuum, a large-sized apparatus is required and the applying plane is fixed. Thus, it is technologically very difficult to activate the artificial hair uniformly over all its surface. In addition, there is a possibility that the artificial hair surface may be largely roughened by the surface treatment, resulting in an artificial hair of reduced quality.

Accordingly, a process for applying an electromagnetic wave such as ionizing radiations or ultraviolet rays, particularly without need for the treatment in vacuum is recommended to produce free radicals. Gamma ($\gamma$) rays or electron beams used as the ionizing radiation are particularly advantageous from a practical standpoint.

The surface modifying treatment can be carried out as a pretreatment for the graft polymerization reaction. However, when the artificial hair produced through the surface modifying treatment is withdrawn into air, the free radicals produced with much effort may be caused to disappear by oxidation in some cases and, hence, it is preferable to use a so-called simultaneous polymerization process in which the graft polymerization is conducted in a liquid phase simultaneously with the surface treatment of the artificial hair.

This simultaneous polymerization process produces radicals on the artificial hair surface to promote the graft-polymerization reaction, thereby introducing graft-polymerized chains into the artificial hair surface, by applying an electromagnetic wave energy such as ionizing radiation and ultraviolet rays in a condition in which the artificial hair has been immersed into a solution containing a radical polymerizable monomer such as a carboxyl group-containing monomer or a sulfonic group-containing monomer.

This process largely prevent the disappearance of radicals by oxidation after modification of the surface. Therefore, the graft polymerization can be advanced with a high efficiency and, moreover, the graft-polymerized chains can be uniformly introduced into the artificial hair surface by applying the actinic radiation to the artificial hair from multiple directions and rotating the artificial hair with respect to the source of light.

However, when the simultaneous polymerization process is used, the following disadvantage is encountered: the absolute amount of the polymer formed is limited, because homopolymerization of the monomer is advanced simultaneously with the graft polymerization onto the artificial hair surface. Therefore, it is preferable that the graft-polymerizing treatment is repeatedly conducted several times.

The graft polymerization can be conducted in the presence of a deoxygenating agent, whereby the reaction time can be shortened and the yield can be increased. If oxygen is present in the monomer solution, the oxygen hinders the graft polymerization, and hence, a deoxygenating agent is desirably added to remove free oxygen from the liquid monomer composition. It is preferable to use riboflavin or periodic acid as such a deoxygenating agent.

The deoxygenating effect of riboflavin or periodic acid is promoted by application of light, particularly, ultraviolet rays.

Examples of the carboxyl group-containing monomer which may be used are acrylic acid, methacrylic acid and the salts and derivatives thereof. Particularly, acrylic acid or methacrylic acid is preferred. Examples of the sulfonic group-containing monomer which may be used are acrylamide methyl propane sulfonate, styrene sulfonate, and the salts and derivatives thereof. Particularly, 2-acrylamide-2-methyl propane sodium sulfonate or styrene sodium sulfate is preferred.

To chemically bond the protein to the graft-polymerized chain introduced into or onto the artificial hair surface in the above manner, a covalent bonding reaction or an ionic bonding reaction can be utilized.

The covalent bonding reaction is utilized effectively for the chemical bonding reaction between the carboxyl group of the graft-polymerized chains and the protein molecules, but is not utilized effectively for the chemical bonding reaction between the sulfonic group of the graft-polymerized chains and the protein molecules.

To covalently bond the carboxyl group of the graft-polymerized chains with the protein molecules, it is required that the carboxyl group is first activated.

When the carboxyl group-containing monomer is used, this activation is achieved by treating the artificial hair which has been surface-modified by the graft polymerization, with an activating agent such as a carbodiimide-based compound or an N-hydroxyl-succinylimide to convert the carboxyl group into an anhydride. The use of 1-ethyl-3-(3-dimethylaminopropyl) carbodiimide as such carbodiimide-based compound is recommended.

When the artificial hair having the carboxyl groups activated by the above described process is immersed in an aqueous solution of a protein, the carboxyl groups converted into the anhydrides and the amino groups of the protein are bonded to each other by covalent bonding, whereby the protein is chemically fixed to the artificial hair surface.

When the ionic bonding reaction is used, a poly-ion complex formation between the anionic groups possessed by the graft-polymerized chains and the cationic groups possessed by the protein is utilized. To perform the poly-ion complex formation, the protein is initially dissolved into an acidic buffered solution with a pH value lower than 7, preferably, an acidic buffered solution with a pH value of 2 to 4 to cationize the protein molecules.

When the artificial hair having the graft-polymerized chain introduced thereinto is immersed in the aqueous solution of the protein, the anionic groups in the graft-polymerized chains and the cationized protein molecules are firmly bonded to each other by ionic bonding and, as a result, the protein is chemically bonded to the artificial hair surface.

Any of the graft-polymerized carboxyl group-containing monomer or the graft-polymerized sulfonic group-containing monomer can be ionically bonded to the protein by the poly-ionic complex formation, but the sulfonic group-containing monomer is more preferred from the viewpoints of the strength of the bond and the ease of the reaction.

The artificial hair having the protein chemically bonded to the surface in the above manner can be satisfactorily used in a practical way. However, if the so-coated artificial hair has been implanted, then it is subjected to a decomposing action by enzymes in the skin tissue over a long period. Thereupon, to inhibit the decomposing action, it is preferable that the fixed protein is further treated by crosslinking.

The crosslinking of the protein molecules can be achieved by utilizing a photo-crosslinking reaction produced by application of ultraviolet rays, or a chemically crosslinking reaction using a reaction promoting agent such as glutaraldehyde and formalin.

In addition to the crosslinking between the protein molecules chemically bonded to the artificial hair, the crosslinking of the protein can also include the crosslinking of the protein chemically bonded to the artificial hair with a protein subsequently additionally added thereto.

When the photo-crosslinking reaction is utilized as a particular method for the crosslinking of the protein, the crosslinking reaction of the protein can be conducted by application of ultraviolet rays for several hours, after the artificial hair having the protein chemically fixed to the surface thereof has been immersed into the aqueous solution of the protein as required, and then pulled up and dried.

When the chemically crosslinking reaction is utilized, the artificial hair having the protein chemically fixed to the surface thereof is immersed into an aqueous solution of formalin or glutaraldehyde after being immersed into the aqueous solution of the protein as required, and then pulled up and dried. If several hours have lapsed while gently stirring the aqueous solution at a relatively low temperature, the crosslinking of the protein is completed, and the artificial hair is withdrawn, washed and then dried.

Particularly, when the graft polymerization is carried out by the simultaneous polymerization process, it is difficult to increase the absolute amount of the fixed protein. Therefore, in crosslinking the protein, it is preferable to additionally add another protein to crosslink the proteins simultaneously.

This method ensures that the film thickness of the protein fixed to the artificial hair surface is increased.

If the resultant artificial hair is implanted in a human skin, it is possible for the artificial hair to have a large resistance to decomposition by the intestine enzyme.

When the graft-polymerization is carried out by the simultaneous polymerization process produced by application of ultraviolet rays or the like, the graft-polymerized chains can be uniformly introduced in the surface of the artificial hair by an inexpensive apparatus without damaging of the surface of the artificial hair. Consequently, it is possible to form the biologically compatible layer containing the protein uniformly fixed in the surface of the artificial hair.

Examples of the protein which may be used in the present invention are collagen, gelatin which is a modified collagen, fibronectin and other cell-bondable proteins. From the viewpoint of biological compatibility, a collagen (which is the primary constituent of the skin tissue) is most preferred.

The graft-polymerized molecule chain bonded to the surface of the artificial hair has a larger size and is less compatible with the polymer from which substrate or body the artificial hair is formed. Therefore, the protein bonded through the graft-polymerized chain does not penetrate into the substrate, and instead the protein is semi-permanently retained in the surface of the artificial hair.

The surface of the artificial hair having the protein fixed by the chemical bonding in this manner has a function as a physiologically active surface. When the artificial hair has been implanted into a human body skin, the biologically compatible layer 11 formed of the protein fixed to the surface of the artificial hair 10 having a hair root 12 as shown in FIG. 1 can be integrally assimilated with and bonded to the proteins in the epidermis 4, corium layer 5, subcutaneous tissue 6 and galea 7, e.g. as shown in FIG.1, whereby the artificial hair becomes firmly fixed.

As a result, the entire artificial hair is fixed in the human body tissue, and there is no gap between the human body tissue and the artificial hair, whereby the danger of infection is greatly reduced. Also, down-growth is prevented by the fact that there is no gap.

BEST MODE FOR CARRYING OUT THE INVENTION

EXAMPLE 1

<First step>: Modification of artificial hair surface

A corona discharge of 9 kV is applied to the surface of an artificial hair produced from a monofilament of a polyamide fiber (nylon-6) for 2 minutes to introduce a peroxide into the artificial hair surface.

<Second step>: Graft polymerization

The artificial hair having the surface modified is immersed into an aqueous solution of acrylic acid. The artificial hair in the aqueous solution is heated at 50° C. for 1 hour while conducting a complete deaeration, thereby graft-polymerizing the acrylic acid monomer to the artificial hair surface.

<Third step>: Removal of homopolymer

Water is supplied to the artificial hair resulting from the graft polymerization at 70° C. for 15 hours to remove any homopolymer which has been produced as an undesired by-product of the second step.

<Fourth step>: Activation of carboxyl group

The artificial hair is immersed for 10 minutes in an aqueous solution of 1-ethyl-3-(3-dimethyl aminopropyl) carbodiimide having a concentration of 10 mg/ml (and having pH=4.5 and a temperature of 4° C.)

<Fifth step>: Covalent bonding of collagen

The artificial hair resulting from the treatment at the fourth step is immersed for 2 hours in an aqueous solution of a collagen ( of the collagen type I of the Nitta Gelatin Co.) having a concentration of 0.5 mg/ml and a temperature of 4° C.

<Sixth step>: Washing

The artificial hair resulting from the fifth step is withdrawn and washed with an aqueous solution of hydrochloric acid of pH 3.0 and then with distilled water.

<Seventh step>: Crosslinking of collagen

The artificial hair resulting from the sixth step and having the collagen fixed thereto is irradiated by a ultraviolet lamp (of 15 W and 254 nm). If the artificial hair is irradiated all over while being rotated, the photo-crosslinking reaction is completed in about 12 hours, thereby providing an artificial hair having the collagen firmly fixed thereto.

The amount of collagen fixed in the physiologically active surface of the artificial hair formed in the above manner was of 8.1 µg/cm$^2$.

EXAMPLE 2

<First step>: Primary graft polymerization

A solution produced by adding 20 mg of riboflavin to a 1% by weight aqueous solution of dimethylaminoethyl methacrylate is placed into a test tube made of quartz, and an artificial hair made from a monofilament of a polyethylene terephthalate fiber is immersed into the solution. Nitrogen gas is blown into the solution and then, the test tube is closely plugged.

The test tube is irradiated by ultraviolet rays for 2 hours while being rotated around its own axis (rotation) and revolved around an axis through a center of the light source (revolution).

As the graft polymerization is advanced, the viscosity of the solution is gradually increased.

At this stage, because of the substantial permeation of the dimethylaminoethyl methacrylate into the artificial hair, the dimethylaminoethyl methacrylate can be graft-polymerized even with the polymer compound at a location of the artificial hair slightly deeper than the surface thereof.

<Second step>: Secondary graft polymerization

Then, the artificial hair resulting from the graft polymerization of the above-mentioned first step is immersed into a solution which has been likewise produced by adding 20 mg of riboflavin to a 5% by weight aqueous solution of acrylic acid placed into a test tube. Nitrogen gas is blown into the solution and then, the test tube is closely plugged. The test tube is irradiated for 2 hours by ultraviolet rays while being rotated around its own axis and revolved around an axis through a center of the light source. When the graft polymerization is advanced, the viscosity of the solution increases.

This step is carried out mainly in order to graft-polymerize more abundantly the anionic monomer on the surface portion of the artificial hair and to neutralize cations liberated at the first step.

<Third step>: Removal of homopolymers

Homopolymers of dimethylaminoethyl methacrylate and acrylic acid are produced at the first and second steps respectively, and will impede the covalent bonding of a collagen at the subsequent step. Therefore, in order to remove the homopolymers, water at 70° C. is supplied for 15 hours to the artificial hair resulting from the first and second step treatment.

<Fourth step>: Activation of carboxyl group

In order to activate the carboxyl groups in the graft chains of polyacrylic acid and polymethacrylic acid produced by the graft polymerization, the artificial hair is immersed for 10 minutes in a 10 mg/ml solution of 1-ethyl-3-(3-dimethyl aminopropyl) carbodiimide (having a pH value of 4.5 and a temperature of 4° C.).

<Fifth step>: Covalent bonding of collagen

When the artificial hair resulting from the treatment at the fourth step is immersed for 1 to 2 hours in an aqueous solution (at 20° C.) of a collagen (collagen-type I of the Nitta Gelatin Co.), the collagen becomes covalently bonded to the carboxyl groups introduced by the graft polymerization and fixed to the artificial hair surface. After completion of the reaction, the resulting artificial hair is withdrawn; washed with a solution of hydrochloric acid of pH 3.0 and then with distilled water and dried at room temperature.

<Sixth step>: Crosslinking of collagen

Glutaraldehyde is dissolved into a buffering agent of phosphoric acid (pH 7.4) or distilled water (pH 6.0) to provide a concentration of 12.5 mM to 200 mM, and the resulting solution is kept at 4° C. The artificial hair resulting from the fifth step and having the collagen fixed thereto is immersed into the solution of glutaraldehyde, and the crosslinking reaction is conducted for 24 hours while gently stirring the solution at 4° C. After the reaction, the resulting artificial hair is washed with distilled water and dried at room temperature.

The amount of collagen fixed to the physiologically active surface of the artificial hair formed in the above manner was of 16 µg/cm².

EXAMPLE 3

<First step>: Graft polymerization

Riboflavin is added in an amount of 4 mg/l to 70 ml of a 1% by weight aqueous solution of 2-acrylamide-2-methyl propane sodium sulfonate. A polyester fiber is inserted into a test tube containing this monomer solution placed therein. Thereafter, nitrogen gas is blown for 30 minutes into the solution, and the test tube is tightly plugged.

The test tube is irradiated for 2 hours by ultraviolet rays while being rotated around its own axis and revolved around an axis through a center of the light source.

<Second step>: Removal of homopolymer

In order to remove sulfonic acid homopolymer, the graft-polymerized artificial hair resulting from the first step is washed with warm water at 70° C. for 15 hours.

<Third step>: Fixing of collagen 0.5 mg/ml of an aqueous solution of collagen (prepared from the collagen type I of Nitta Gelatin Co. at pH 3 using hydrochloric acid) is placed into a test tube, and the graft-polymerized artificial hair resulting from the second step is immersed into the solution in the test tube. When the artificial hair is left to stand over night, the collagen becomes fixed to the artificial hair surface by an ionic bonding reaction. The resulting artificial hair is withdrawn; washed with hydrochloric acid and then with distilled water, and finally dried at room temperature.

<Fourth step>: Crosslinking of collagen

The artificial hair resulting from the third step and having the collagen fixed to the surface thereof is immersed into 1.5 mg/ml of an aqueous solution of a collagen (having a pH value of 3.0); dried and irradiated all over at room temperature for 12 hours by a ultraviolet lamp (of 15 W and 254 nm) while being rotated, thereby crosslinking the collagen.

Further, the resulting artificial hair is immersed into 3 mg/ml of an aqueous solution of a collagen (having a pH value of 3.0); then dried and irradiated all over at room temperature for 24 hours by a ultraviolet lamp (of 15 W and 254 nm) while being rotated, thereby crosslinking the collagen to provide an artificial hair having the collagen firmly fixed to the surface thereof.

The amount of the collagen fixed to the physiologically active surface of the artificial hair formed in the above manner was of 35.6 µg/cm².

INDUSTRIAL APPLICABILITY

Since the biologically compatible layer is formed by chemical bonding of the protein to the surface of the artificial hair made from a monofilament of a synthetic fiber such as polyethylene, polypropylene, polyester, polyamide, acrylic and fluorine-based fibers, fibroblasts in the epidermis, corium and subcutaneous tissue are deposited to the protein layer of the surface of the implanted artificial hair after a lapse of a given period of time, and the protein layer is assimilated to the protein produced from such fibroblasts.

Therefore, when the artificial hair is implanted into human head skin, the the biologically compatible layer of the artificial hair is bonded with the subcutaneous tissue and the implanted artificial hair Consequently, it can be provided the artificial hair for implantation having characteristics such as a low infection rate against a suppurative germ, a high success rate of implanted artificial hairs and no occurrence of a down-growth phenomenon.

We claim:

1. A process for producing an artificial hair for implantation, formed from a monofilament of a synthetic polymer fiber, said process comprising the steps of:

introducing a graft-polymerized polymer chain onto a surface of the artificial hair by applying ionizing radiation or ultraviolet rays which produce free radicals in the surface of the artificial hair under a condition in which the artificial hair has been immersed in a solution of a radical-polymerizable monomer selected from the group consisting of a carboxyl group-containing monomer and a sulfonic group-containing monomer;

chemically bonding protein molecules to said graft-polymerized chain; and bonding the protein molecules chemically bonded to said graft-polymerized chain to one another, or to additionally added protein molecules by cross-linking to form a biologically compatible layer on the surface of the artificial hair.

2. A process for producing an artificial hair for implantation, formed from a monofilament of a synthetic polymer fiber, said process comprising the steps of introducing graft-polymerized polymer change onto a surface of the artificial hair in the presence of a deoxygenating agent;

chemically bonding protein molecules to said graft-polymerized chain; and bonding the protein molecules chemically bonded to said graft-polymerized chain to one another, onto additionally added protein molecules by cross-linking to form a biologically compatible layer on the surface of the artificial hair.

3. A process for producing an artificial hair for implantation, formed from a monofilament of a synthetic polymer fiber, said process comprising the steps of introducing a graft-polymerized polymer chain onto a surface of the artificial hair;

chemically bonding protein molecules to said graft-polymerized chain by utilizing an ionic bonding reaction; and bonding the protein molecules chemically bonded to said graft-polymerized chain to one another, onto additionally added protein molecules by cross-linking to form a biologically compatible layer on the surface of the artificial hair.

4. In an artificial hair for implantation, formed from a monofilament of a synthetic polymer fiber and having a loop (12) and a hook (13) at one end thereof, the improvement wherein said artificial hair includes a biologically compatible layer on an outer surface thereof, said biologically compatible layer comprising a protein fixed to said synthetic polymer by chemical bonding.

5. A process for producing an artificial hair for implantation according to claim 1, wherein the protein is chemically bonded to said graft-polymerized chain by utilizing a covalent bonding reaction.

6. A process for producing an artificial hair for implantation according to claim 5, wherein said covalent bonding reaction is promoted by activating said graft-polymerized chain by an activating agent.

7. A process according to claim 6, wherein said activating agent is a carbodiimide compound or N-hydroxylsuccinimide.

8. A process for producing an artificial hair for implantation according to claim 2, wherein said deoxygenating agent used is riboflavin or periodic acid.

9. A process for producing an artificial hair for implantation according to claim 1, wherein said carboxyl group-containing monomer used is one or more monomers selected from the group consisting of acrylic and methacrylic acids and the salts and derivatives thereof.

10. A process for producing an artificial hair for implantation according to claim 1, wherein said sulfonic group-containing monomer used is one or more monomers selected from the group consisting of acrylamidemethyl propane sulfonic acid and styrene sulfonic acid and the salts and derivatives thereof.

11. A process for producing an artificial hair for implantation according to claim 3, wherein the pH value of a solution resulting from the reaction between said graft-polymerized chain and said protein is adjusted to a value in a range of 2 to 7 to promote said ionic bonding reaction.

* * * * *